United States Patent [19]

Fabregat

[11] Patent Number: 5,313,973

[45] Date of Patent: * May 24, 1994

[54] INSTALLATION FOR THE SUPPLY OF OXYGEN TO HOSPITALS AND THE LIKE

[75] Inventor: Francisco B. Fabregat, Boadilla del Monte, Spain

[73] Assignee: Dessarollos, Estudios & Patentes, S.A., Madrid, Spain

[ * ] Notice: The portion of the term of this patent subsequent to Feb. 12, 2008 has been disclaimed.

[21] Appl. No.: 591,607

[22] Filed: Oct. 2, 1990

Related U.S. Application Data

[63] Continuation of Ser. No. 295,806, Jan. 11, 1989, Pat. No. 4,991,616.

[30] Foreign Application Priority Data

Jan. 11, 1988 [ES] Spain .................................. 8800056

[51] Int. Cl.$^5$ ............................................ A61M 16/12
[52] U.S. Cl. .................................. 137/3; 128/204.29; 137/93
[58] Field of Search ...................... 137/3, 88, 93, 113, 137/114; 128/203.25, 204.22, 204.29, 205.11, 205.12

[56] References Cited

U.S. PATENT DOCUMENTS

| | | |
|---|---|---|
| 2,547,823 | 4/1951 | Josephian .......................... 137/114 X |
| 2,582,848 | 2/1958 | Price . |
| 2,824,557 | 2/1958 | Mejean et al. . |
| 2,877,966 | 3/1959 | Summers . |
| 3,204,653 | 9/1965 | Hettlinger . |
| 3,215,057 | 11/1965 | Turek . |
| 3,410,191 | 11/1968 | Jackson . |
| 3,425,333 | 2/1969 | Wachter . |
| 3,500,827 | 3/1970 | Paine . |
| 3,526,239 | 9/1970 | Oroza .............................. 137/114 X |
| 3,593,735 | 7/1971 | Reiher . |
| 3,720,501 | 3/1973 | Cramer et al. . |
| 3,896,837 | 7/1975 | Rohling .......................... 137/113 X |
| 3,957,043 | 5/1976 | Shelby ............................. 137/88 X |
| 4,057,205 | 11/1977 | Vensel . |
| 4,072,148 | 2/1978 | Munsen et al. .................. 128/205.11 |
| 4,364,493 | 12/1982 | Raynes et al. ................... 137/114 X |
| 4,419,926 | 12/1983 | Cronin et al. . |
| 4,428,372 | 1/1984 | Beysel et al. ................ 128/205.12 X |
| 4,499,914 | 2/1985 | Schebler . |
| 4,627,860 | 12/1986 | Rowland ..................... 128/204.22 X |
| 4,651,728 | 3/1987 | Gupta et al. ................ 128/204.29 X |

FOREIGN PATENT DOCUMENTS 2532858 3/1984 France .
2130402 5/1984 United Kingdom .

Primary Examiner—Stephen M. Hepperle
Attorney, Agent, or Firm—Davis Hoxie Faithfull & Hapgood

[57] ABSTRACT

An installation for the supply of oxygen including an oxygen source and an oxygen generating unit, where oxygen is supplied simultaneously to a mixing frame from the oxygen source and oxygen generating unit. An emergency frame may be included as well.

26 Claims, 2 Drawing Sheets

INSTALLATION FOR THE SUPPLY OF OXYGEN TO HOSPITALS AND THE LIKE

The present invention is a continuation of U.S. Ser. No. 07/295,806, filed Jan. 11, 1989 which was allowed on Jun. 8, 1990 as U.S. Pat. No. 4,991,616.

FIELD OF THE INVENTION

The present invention relates to an installation for the supply of oxygen in hospitals and the like which is highly reliable and provides a substantial economic savings.

BACKGROUND OF THE INVENTION

Oxygen is the most abundant element in nature. It forms approximately 21% of the atmosphere. It is bonded to hydrogen in water and it is found forming part of most minerals and rocks. It is a constituent of all living beings and is essential for ensuring the organic metabolism of animals. In superior vertebrates, such as man, oxygen is inhaled through the lungs and then subsequently transported through the bloodstream.

A basic life-supporting element, it is not surprising that oxygen is also essential in many medicinal applications. Many medical processes require this element as an agent to speed up metabolism. Oxygen therapy and air therapy are well known examples. Oxygen is also used in anesthesia, as well as in open heart surgery, where the patient's blood must be directly oxygenated. Oxygen, therefore, is may not be lacking in any hospital and is consumed in large amounts.

In order to ensure this supply and to enable its distribution throughout the hospital complex, a supply station typically distributes the product throughout the hospital through an internal distribution network. The supply station is usually composed of steel cylinders (bottles) which contain the gas under pressure. More recently, cryogenic tanks are used to store liquid oxygen at low temperature. After vaporization in a heat exchanger, the oxygen is supplied to the hospital network. All the stations have corresponding emergency systems, such as a set of bottles which act as a reserve and enter into operation in case of need should the main source suffer a serious breakdown or should there be no supply.

Medicinal oxygen is an expensive product whose price is determined by two factors. First, it is necessary that its purity be high, approximately 99.9%. It is also essential to ensure that oxygen for hospital consumption is not in any way polluted.

Second, consumption of the product by an average hospital is considerably smaller than in industrial consumption. The installations required for its storage, specifically in the case of cryogenic tanks, have similar and considerably higher costs, which have a more significant effect in the price of medicinal oxygen.

The medicinal application of pure oxygen is practically non-existent. In fact, pure oxygen is a highly toxic product and its continued inhalation causes death. It is therefore normally supplied with air or other gases in variable concentrations which very rarely exceed 80%. Most frequently, the oxygen product is provided in a proportion of around 40%. For this reason, American Pharmacopoeia has just authorized the classification of medicinal oxygen as oxygen which does not have an impurity of inert gases of over 7%, and therefore a concentration of oxygen equal to or over 93%.

The possibility of "filtering" air, separating its constituents, was achieved some years ago by means of zeolite filters or membranes, which absorb a gas (generally nitrogen) and allow the rest to pass through. Thus oxygen may be produced, in situ, with a considerably low cost by a system of compressors and filters. This requires reduced maintenance and low consumption of energy.

The main disadvantage of these units is that they cannot produce oxygen with a purity of over 95%. The need for such purity, however, has been eliminated with the recent authorization of American Pharmacopoeia. The required 93% purity is easily obtained with the main remaining impurity being the inert gas argon.

It is wholly unthinkable that a hospital may be deprived of the oxygen supply. This condition must be avoided at all costs and any supply system must absolutely prevent this. Autonomous generating units are not satisfactory because they are machines subject to possible breakdowns and stoppings.

By duplicating some parts of the system, it is possible to decrease the risk of stoppage, but, apart from the fact that total elimination of the risk thereof is impossible, successive accumulation of duplicate or safety elements make the costs of these units so high that the oxygen produced no longer has economic advantages.

SUMMARY OF THE INVENTION

The installation for the supply of oxygen of the present invention comprises an oxygen source, an oxygen generating unit, and a mixing frame for mixing oxygen simultaneously supplied by the oxygen source and the oxygen generating unit.

More specifically, the installation comprises an oxygen source or station of the conventional type, either based on bottles or by means of a cryogenic container, and of an oxygen generating unit through the likewise conventional method of filtering. From these two basic means for obtaining oxygen, a mixing frame is established. A middle mixture deposit may lie behind the mixing frame. An emergency frame which allows the normal connection to the supply network of the middle mixture deposit to be substituted by the connection to an emergency set may also be provided.

In another aspect of the invention, the installation for the supply of oxygen comprises an oxygen source, an oxygen generating unit, a mixing frame for mixing oxygen simultaneously supplied by the oxygen source and the oxygen generating unit, an emergency frame for receiving the mixture of oxygen and detecting a drop in pressure below a pre-established limit and an emergency oxygen supply to supply oxygen to the emergency frame if the emergency frame detects a drop in pressure.

PREFERRED EMBODIMENT OF THE INVENTION

Figure 1:
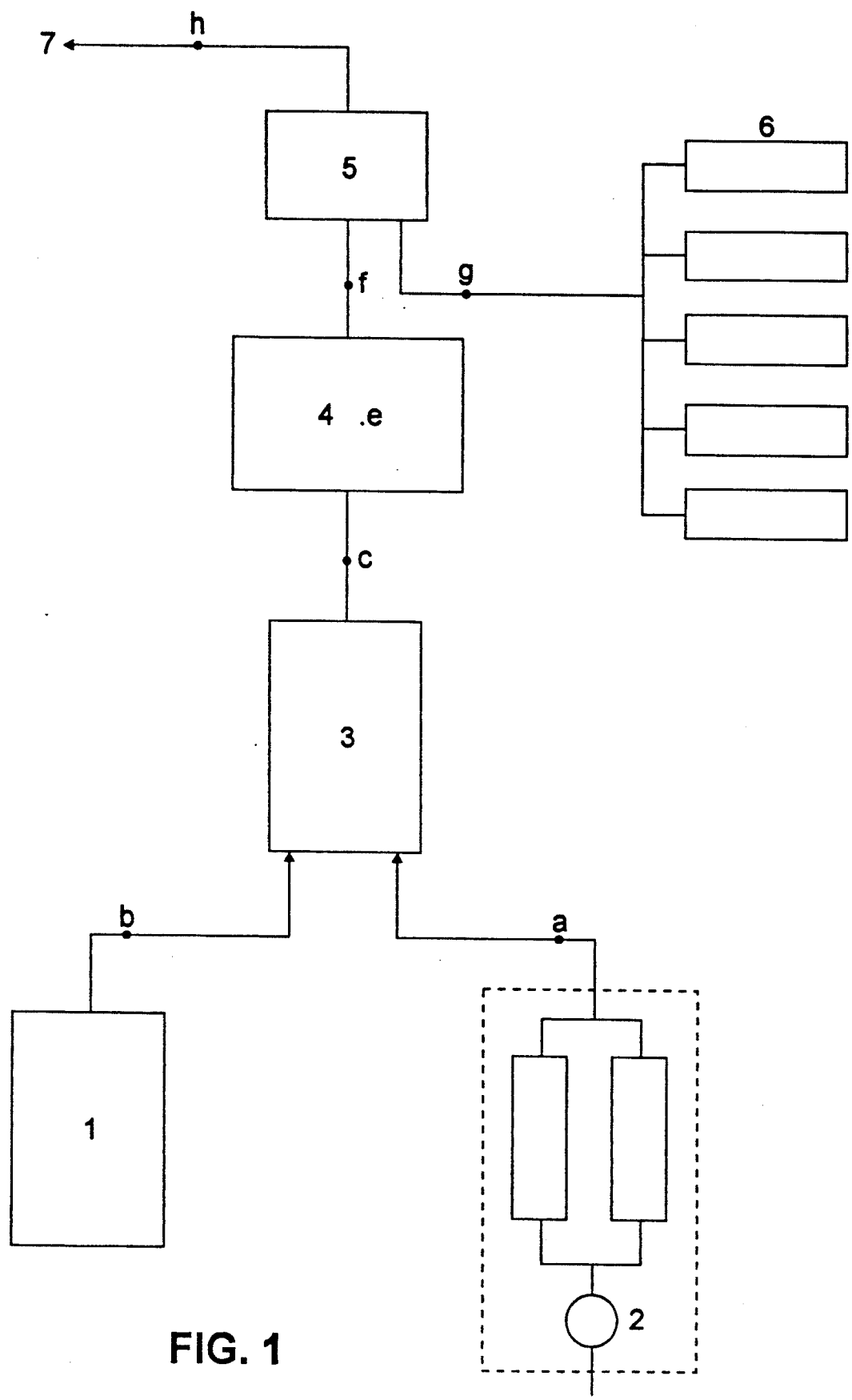
FIG. 1 is a block diagram of an installation for the supply of oxygen in hospitals and the like, in accordance with the object of the present invention.

In FIG. 1, the installation comprises an oxygen source or station 1, being of a conventional type, either of bottles or else materialized in a cryogenic container, and a unit 2 for the generation of oxygen through the conventional method of filtering. The oxygen station 1 and generating unit 2 are connected to a mixing frame 3, from which the oxygen is led to a middle mixture deposit 4. Behind the middle mixture deposit in the preferred embodiment is an emergency frame 5 which allows automatic connection of an emergency set 6 to the installation 7 in the event of a scarcely probable, but possible, emergency.

More specifically, oxygen source 1 supplies oxygen to mixing frame 3 with a flow $Q_1$ and a concentration $Cn_1$, which is practically 100%, whereas generating unit 2 supplies a flow $Q_2$ with a concentration $Cn_2$ to the same frame 3. Both streams of gas are mixed in frame 3. A flow $Q_3$ is obtained which is the result of adding $Q_1$ and $Q_2$, resulting in a gas with a concentration $Cn_3$:

$$Cn_3 = \frac{Cn_1 Q_1 + Cn_2 Q_2}{Q_1 + Q_2}$$

The mixture is introduced in the middle deposit 4, which has a considerable capacity, and which acts as a homogenizer and pressure equalizer. From here the mixture goes through emergency frame 5 to distribution network 7.

The emergency frame 5 detects a possible drop in pressure in the container to below a pre-established minimum limit, which would give rise to the interruption of the flow $Q_3$. After such detection, oxygen from emergency set 6 is supplied to the emergency frame 5.

Figure 2:
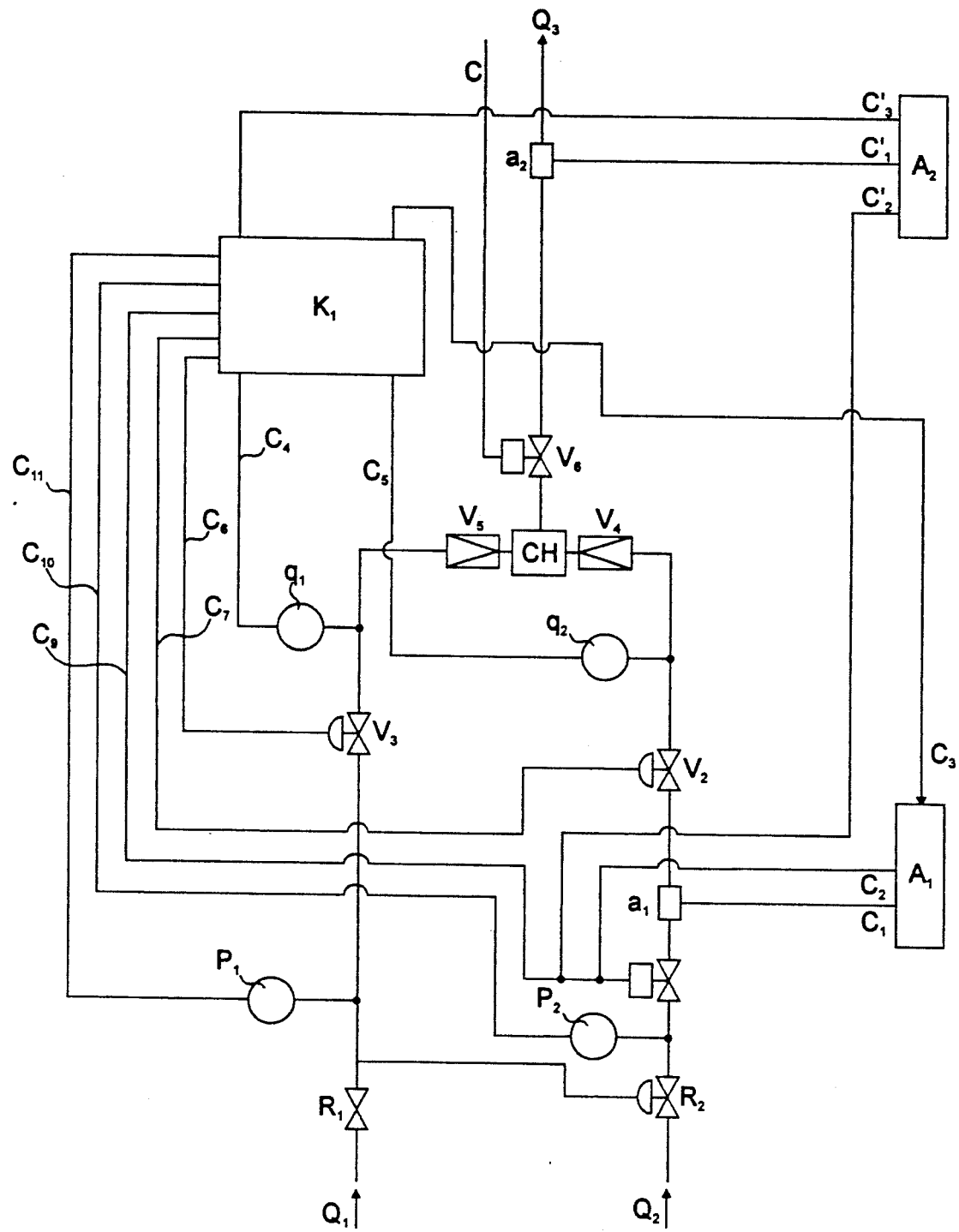
FIG. 2 is a diagrammatic representation of the mixing frame installation of FIG. 1.

The mixing frame 3 is shown in greater detail in FIG. 2. The gas from the oxygen station flows through a pressure controller $R_1$, a control valve $V_3$, a single way valve $V_5$, and then into a small mixing chamber CH. The gas from the oxygen generating station similarly flows through a pressure controller $R_2$, a control valve $V_2$, a single way valve $V_4$ and finally into the small mixing chamber CH.

The minimum values of oxygen concentration considered to be acceptable are introduced into oxygen analyzers $A_1$ and $A_2$. The controller $K_1$ determines the proportion between flows which must exist between line 1 and 2 (i.e., between $Q_1$ and $Q_2$). It should be borne in mind that the information in $A_2$ is not independent, but is determined by the formula:

$$Cn_3 = \frac{Cn_1 Q_1 + Cn_2 Q_2}{Q_1 + Q_2}.$$

If $Q_1/Q_2 = X$ $$Cn_3 = \frac{Cn_1 X + Cn_2}{1 + X}.$$

If we consider that very approximately $Cn_1 = 100$, than $$Cn_3 = \frac{100 X + Cn_2}{1 + X}.$$

The controller $K_1$, measuring flows through flow transducers $q_1$ and $q_2$, regulates the apertures of the control valves of $V_2 V_3$ to obtain the mixing relation X, with a minimum predetermined flow of, for example, $Q_1$. The oxygen station/oxygen generator gas mixture, after being made in the small chamber CH and sensed by oxygen concentration sensor $a_2$, is led to container 4 and, from here, to the distribution network.

Should, due to some anomaly, pressure sensors $p_1$ and $p_2$ detect different pressures which might affect the mixture, controller $K_1$ would close electrovalve $V_1$, and the network would be fed only from oxygen station 1. Should $A_1$ detect a concentration below that expected through control line $C_1$ from oxygen concentration sensor $a_1$, $A_1$ would close $V_1$ through control line $C_2$. Upon closing $V_1$, $A_1$ would also inform $K_1$ through control line $C_3$ that 100% of the flow should come from the oxygen station 1.

Similarly, should $A_2$ detect a concentration below that expected from oxygen concentration sensor $a_2$ through control line $C_1'$, $A_2$ would close $V_1$ through control line $C_2'$. Upon closing $V_1$, $A_2$ would also inform $K_1$ through control line $C_3'$ that 100% of the flow should come from the oxygen station 1.

Two analyzers are preferred for safety. It is possible to construct cheap oxygen analyzers based on simple chemical sensors but they have the disadvantage of a reduced stability and duration. The existence of two banked units requires a condition of simultaneous triple failure (which is practically impossible: oxygen generator and the two analyzers) for the irregular operation of the unit. Finally, in the event of actuation of frame 5, the latter activates electrovalve $V_6$ simultaneously with the introduction of the set of bottles. In the event of failure of the system of the present invention, the only effect will be greater consumption from the traditional source. This allows us to install a simple and cheap generating source.

The efficiency of the generators decreases significantly when oxygen is desired with a maximum concentration of 95%. It is therefore convenient not to surpass values of 90%. Under these conditions, the cost of the oxygen including energy consumption, which a generating unit may produce is of around ¼ of the cost of the traditional medicinal oxygen. The following table may be established, wherein $Cn_2$ represents the oxygen concentration of the gas from the oxygen source, $Cn_3$ represents the final concentration of the oxygen, $P_3$ represents the price of the final product and $P_1$ represents the price of oxygen supplied by an external supplier. In the table below, $Cn_1$ equals 100% and $Cn_2$ equals 90%. $P_3$, the price of the final product, is determined by the equation below:

$$P_3 = \frac{P_1 (X + 0.25)}{(1 + X)}$$

| X | = | $Q_1/Q_2$ | $Cn_3$ | $P_3$ | |
|---|---|---|---|---|---|
| 4 | = | (80/20) | 98% | 0.85 | $P_1$ |
| 1.5 | = | (60/40) | 96% | 0.7 | $P_1$ |
| 1.0 | = | (50/50) | 95% | 0.625 | $P_1$ |
| 0.67 | = | (40/60) | 94% | 0.55 | $P_1$ |
| 0.43 | = | (30/70) | 93% | 0.47 | $P_1$ |

This installation is highly reliable, virtually eliminating the risk of a loss of oxygen supply. The reduction in the costs of the system can reach 50%, while the oxygen concentration is only reduced 7%.

The unit has been described as being appropriate for hospital use, but it is obvious that it could be used in any other case wherein oxygen with a guaranteed quality, continuous supply and low price were required.

I claim:

1. An installation for the supply of oxygen comprising an oxygen source; an oxygen generating unit; a means for mixing oxygen simultaneously supplied by said oxygen source and said oxygen generating unit to said means in a desired proportion, said means being separate from said oxygen source and oxygen generating unit; and means for preventing oxygen from said oxygen generating unit from entering said oxygen source.

2. The installation of claim 1, further comprising an emergency frame for receiving said mixture of oxygen and detecting a drop in pressure below a pre-established limit; and an emergency oxygen supply connected to said emergency frame, said emergency oxygen supply being activated to supply oxygen to said emergency frame if said emergency frame detects a drop in pressure, said emergency frame supplying said mixture of oxygen to a distribution network.

3. The installation of claim 1, wherein said oxygen source is at least one bottle.

4. The installation of claim 1, wherein said oxygen source are cryogenic tanks.

5. The installation of claim 1, wherein the oxygen generating unit provides oxygen through the filtering of air.

6. The installation of claim 1, wherein the concentration of oxygen supplied by the oxygen source and the oxygen generating unit are different. said mixing frame and supplying said mixture to said emergency frame.

7. The installation of claim 1, wherein the mixing frame further comprises two pressure sensors, one for measuring the pressure of oxygen from the oxygen source and the other for measuring the pressure of oxygen from the oxygen generating unit.

8. The installation of claims 7, further comprising two pressure controllers for ensuring that the outlet pressures from the oxygen source and oxygen generating unit are the same.

9. The installation of claim 1, wherein the concentration of oxygen supplied by the oxygen source is about 100% and the concentration of oxygen supplied from the oxygen generating unit is greater than about 90%.

10. The installation of claim 1, wherein the means for mixing is a mixing frame.

11. The installation of claim 10, further comprising a middle mixture deposit station for receiving said mixture of oxygen from said mixing frame and supplying said mixture to said emergency frame.

12. The installation of claim 11, wherein said mixing frame mixes the concentrations of oxygen supplied by the oxygen source and oxygen generating station such that the mixture of oxygen supplied to the middle mixture deposit is homogeneous and at pressure equilibrium.

13. The installation of claim 10, wherein the mixing frame comprises two oxygen analyzers, one for determining the concentration of oxygen from the output of the mixing frame, and the other for determining the concentration of oxygen from the oxygen generating unit.

14. The installation of claim 13, wherein the minimum acceptable values for the oxygen concentration are stored in the analyzers.

15. The installation of claim 13, wherein the mixing frame further comprises a controller for controlling the proportion between the oxygen flow from the oxygen source and the oxygen flow from the oxygen generating unit.

16. The installation of claim 10, wherein the mixing frame further comprises a small mixing chamber for mixing the oxygen from the oxygen source and the oxygen generating unit.

17. An installation for the supply of oxygen comprising an oxygen source, an oxygen generating unit, a mixing frame separate from said oxygen source and oxygen generating unit for mixing oxygen simultaneously supplied to said mixing frame by said oxygen source and said oxygen generating unit in a desired proportion, means for preventing oxygen from said oxygen generating unit from entering said oxygen source, an emergency frame for receiving said mixture of oxygen and detecting a drop in pressure below a preestablished limit and an emergency oxygen supply to supply oxygen to said emergency frame if said emergency frame detects a drop in pressure.

18. A method for the supply of oxygen comprising the steps of simultaneously providing oxygen from an oxygen source and an oxygen generating unit to a mixing frame separate from said oxygen source and oxygen generating unit, mixing said oxygen in a desired proportion and preventing oxygen from said oxygen generating unit from entering said oxygen source.

19. The method of claim 18 further comprising providing said mixture of oxygen to an emergency frame, monitoring the pressure of said oxygen in said emergency frame and providing oxygen from an emergency oxygen supply to said emergency frame if insufficient pressure is detected in said emergency frame.

20. The method of claim 18, wherein said mixing is performed in a mixing frame.

21. The method of claim 18, wherein the concentration of oxygen provided by the oxygen source and the oxygen generating unit are different.

22. The method of claim 20, further comprising analysing the concentration of oxygen from the output of the mixing frame, and analysing the concentration of the oxygen from the generating unit.

23. The method of claim 22, further comprising determining whether a minimum acceptable value for each said concentration has been attained.

24. The method of claim 23, further comprising controlling the proportion of flow from the oxygen source and from the oxygen generating unit.

25. The method of claim 18, further comprising measuring the pressure of oxygen from the oxygen source and measuring the pressure of oxygen from the oxygen generating unit and controlling the outlet pressures from the oxygen source and the oxygen generating unit so that said pressures are the same.

26. The method of claim 18, wherein the concentration of the oxygen provided from the oxygen source is about 100% and the concentration of oxygen provided from the oxygen generating unit is greater than about 90%.

* * * * *